United States Patent [19]

Ellis, Jr. et al.

[11] Patent Number: 5,280,115
[45] Date of Patent: Jan. 18, 1994

[54] NITRATED METALLOPORPHYRINS AS CATALYSTS FOR ALKANE OXIDATION

[75] Inventors: Paul E. Ellis, Jr., Downingtown; James E. Lyons, Wallingford, both of Pa.

[73] Assignee: Sun Company, Inc. (R&M), Philadelphia, Pa.

[21] Appl. No.: 892,106

[22] Filed: Jun. 2, 1992

Related U.S. Application Data

[63] Continuation-in-part of Ser. No. 758,147, Sep. 12, 1991, Pat. No. 5,120,882.

[51] Int. Cl.$^5$ .......................................... C07D 487/22
[52] U.S. Cl. ................................................ 540/145
[58] Field of Search ........................................ 540/145

[56] References Cited

U.S. PATENT DOCUMENTS

| | | | |
|---|---|---|---|
| 4,822,899 | 4/1989 | Groves et al. | 540/145 |
| 4,892,941 | 1/1990 | Dolphin et al. | 540/145 |
| 4,895,680 | 1/1990 | Ellis, Jr. et al. | 260/410.9 |
| 4,895,682 | 1/1990 | Ellis, Jr. et al. | 260/410.9 |
| 4,900,871 | 2/1990 | Ellis, Jr. et al. | 568/399 |
| 4,970,348 | 11/1990 | Ellis, Jr. et al. | 568/399 |
| 5,077,394 | 12/1991 | Dolphin et al. | 530/505 |
| 5,120,882 | 6/1992 | Ellis, Jr. et al. | 568/910 |

OTHER PUBLICATIONS

Chikira et al. CA90(15): 120537k (1978).
Chikira et al. J. Chem. Soc., Chem. Commun. (21), 906-7 (1978).
Crossley et al. Tetrahedron, vol. 43, No. 20, pp. 4569-4577 (1987).
R. Bonnett et al., J. Chem. Soc., 30, 2791-2798 (1965).
E. C. Johnson et al., Tetr. Lett. 26, 2197-2200 (1976).
L. C. Gong et al., Cam. J. Chem. 63, 401-405, (1985).
J. E. Baldwin et al., Tetrahedron, 38, 685-692 (1982).
M. Catalano et al., J. Chem. Soc. Chem. Commun., 1535-1536 (1984).

Primary Examiner—Marianne M. Cintins
Assistant Examiner—John Peabody
Attorney, Agent, or Firm—Q. Todd Dickinson

[57] ABSTRACT

Compositions of matter comprising nitro-substituted metal complexes of porphyrins are catalysts for the oxidation of alkanes. The metal is iron, chromium, manganese, ruthenium, copper or cobalt. The porphyrin ring has nitro groups attached thereto in meso and/or β-pyrrolic positions.

14 Claims, No Drawings

NITRATED METALLOPORPHYRINS AS CATALYSTS FOR ALKANE OXIDATION

The Government of the United States of America has rights in this invention pursuant to Cooperative Agreement No. DE-FC21-90MC26029 awarded by the U.S. Department of Energy.

This application is a continuation-in-part of application Ser. No.07/758,147, filed Sep. 12, 1991, now U.S. Pat. No. 5,120,882.

BACKGROUND OF INVENTION

This invention relates to metalloporphyrins useful as catalysts for the oxidation of alkanes, and more particularly to metalloporphyrins containing nitro groups on the porphyrin ring.

Nitro-substituted metalloporphyrins are known in the art. R. Bonnett et al, J. Chem. Soc., 30, 2791-2798 (1965) disclose a nickel complex of α-nitrooctaethylporphyrin, and also uncomplexed α,β,γ-trinitrooctaethylporphyrin. E. C. Johnson et al, Tetr. Lett. 26, 2197 (1976) disclose a magnesium complex of 5,10,15,20-tetranitrooctaethylporphine. L. C. Gong et al, Com. J. Chem., 63, 401-405 (1985), disclose zinc complexes of mono-, di-, tri- and tetra-nitrooctaethylporphyrins. J. E. Baldwin et al, Tetrahedron, 38, 685 (1982), disclose a zinc complex of dinitrotetraphenylporphine. M. Catalano et al, J. Chem, Soc. Chem. Commun., 1535-1536 (1984) disclose nickel, palladium, copper, cobalt, iron, magnesium and zinc complexes of betanitromesotetraarylporphyrins containing in some instances one and in some instances two nitro groups.

The complexes of the Bonnett, Johnson and Gong disclosures above have octaethyl groups at the β-pyrrolic positions of the porphyrin ring and nitro groups at the meso positions of the ring. The complexes of the Baldwin and Catalano disclosures have aryl, e.g. phenyl, groups at the meso positions of the ring, and nitro groups at one or two β-pyrrolic positions of the ring.

U.S. Pat. No. 5,077,394, issued Dec. 31, 1991 to D. H. Dolphin et al, from an application Ser. No. 455,663 filed Dec. 21, 1989 as a division of application Ser. No. 181,859, Apr. 15, 1988, U.S. Pat. No. 4,892,941, which was a continuation-in-part of Ser. No. 39,566, Apr. 17, 1987, abandoned, discloses tetraphenyl porphyrins which are beta-substituted by fluoro or chloro and bear electronegative substituents, for example nitro substituents, on the phenyl.

DESCRIPTION OF THE INVENTION

We have discovered novel nitro-substituted metalloporphyrins which contain nitro groups in meso and/or beta positions of the porphyrin ring.

The atoms or groups on the meso positions of a metalloporphyrin are represented by the X's in the following structural formula, and the atoms or groups on the β-pyrrolic, or beta, positions by the Y's:

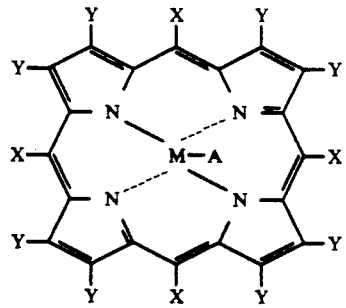

where M is metal, A (1) is an anion such as chloride, bromide, cyanide, azide, nitride, thiocyanate, cyanate, hydroxy, methoxy, chlorate, carboxylates such as acetate, propionate and benzoate, or (2) is absent, said compounds including iron complexes of μ oxo dimers wherein two structures as shown in said formula are joined through an M-O-M linkage.

COMPLEXES OF CERTAIN METALS WITH MESONITROPORPHYRINS

In one embodiment, the invention is an iron, chromium, ruthenium, manganese, copper or cobalt complex of a metalloporphyrin which has one or more nitro groups, $NO_2$, in meso positions. Typically, the compound has, in beta positions, either hydrogen atoms, H, or halogen atoms such as fluorine, chlorine or bromine, or nitro or cyano groups, or a hydrocarbon group or a halocarbon group. Examples of halocarbon groups are haloalkyl groups such as perfluoromethyl, perfluoroethyl and the like, and haloaryl groups such as perfluorophenyl and the like. Examples of hydrocarbon groups are aryl groups such as phenyl, substituted phenyl and the like, and alkyl or cycloalkyl groups such as methyl, ethyl, cyclohexyl and the like.

In this embodiment, 1 to 4 of the X's in the above formula are $NO_2$, 0 to 3 of said X's are hydrogen, halogen, cyano, hydrocarbon or halocarbon, and Y is hydrogen, nitro, cyano, halogen, hydrocarbon or halocarbon. The Y's may all be one atom or group, or different atoms or groups.

The metalloporphyrins of this embodiment differ from the nickel, magnesium or zinc complexes of mesonitrooctaethylporphyrin of the prior art in the metal component of the complex, the nickel, magnesium and zinc complexes being inactive for alkane oxidation, and in some cases by having in beta positions of the porphyrin ring, hydrogen, halogen, halocarbon, cycloalkyl or aryl, rather than the ethyl groups of the prior art compounds.

METAL COMPLEXES OF BETANITROPORPHYRINS

In another embodiment of the invention, the metalloporphyrin has one or more nitro groups in beta positions and hydrogen or a substituent other than nitro in the remaining beta positions. The substituent may be halo, cyano, hydrocarbon or halocarbon.

In this embodiment, X in the above formula is hydrogen, halogen, nitro, cyano, alkyl, cycloalkyl or halocarbon, at least one of said Y's is nitro, and the remaining Y's are hydrogen, halogen, nitro, cyano, hydrocarbon or halocarbon.

In a preferred embodiment, the compound has either halogen atoms or nitro groups in all of the beta positions. In this embodiment, X in the above formula is hydrogen, nitro, cyano, hydrocarbon or halocarbon, at least one of the Y's is nitro and all of the Y's are either nitro or cyano.

This embodiment differs from the meso-tetraphenyl mono- and di-nitroporphyrins of the Catalano et al article supra in having halogens in meso positions.

Substituents in the meso positions of the metalloporphyrins of this embodiment may be aryl groups such as phenyl, or they may advantageously be perhalocarbon groups such as perfluoromethyl, perfluoroethyl and the like. In this embodiment, X in the above formula is a perhalocarbon group, and Y is hydrogen or nitro, at least one of the Y's being nitro.

This embodiment differs from the meso-tetraphenyl nitroporphyrins of the Catalano et al article in having perhalocarbon groups in meso positions of the porphyrin ring.

In each embodiment of the invention, M in the above formula is preferably Fe, Cr, Mn, Ru, Cu or Co, more preferably Fe.

The compounds of the invention are useful, for example, as catalysts in the oxidation of organic compounds. The manner of usage of the compounds for this purpose is disclosed in applicants' copending application, Ser. No. 07/758147, filed Sep. 12, 1991, the disclosure of which is hereby incorporated by reference in this application.

The terms, porphyrin, porphin and porphine are used interchangeably herein to designate the structure shown in the structural formula supra.

The following examples illustrate the invention:

EXAMPLE 1

Preparation of $CuP(NO_2)_4$ (Cu mesotetranitroporphin)

0.5 g of CuP (copper porphin) is dissolved in 300 ml of $CH_2Cl_2$. Through this solution is bubbled $NO_2$ gas for 5 minutes. (This is an excess-lesser amounts to stoichiometric amounts are also sufficient.) The reaction is stirred at room temperature until the Soret band in the ultraviolet of a sample reaches 427 nm. The material can be purified by column chromatography on a 3" by 2" neutral alumina column eluting with $CHCl_3$. The product can also be recrystallized from hot tetrahydrofuran (THF). UV/vis 427, 546, 596 nm ($CHCl_3$). Mass spectrum shows parent peak at 551.8.

EXAMPLE 2

Preparation of Fe Mesotetranitroporphin Chloride $FeP(NO_2)_4Cl$ 0.25 g of FePCl prepared by the metallation of $H_2P$ with $FeCl_2$ in THF is dissolved in 200 ml of $CH_2Cl_2$ and excess $NO_2$ is bubbled through the solution for 5 minutes. After a few minutes of stirring the Soret band shifts from 396 nm to 428 nm. The $CH_2Cl_2$ is removed by evaporation and the impure $NO_2$ complex is purified by column chromatography on neutral alumina or recrystallization in hot THF.

EXAMPLE 3

$ZnP(NO_2)_4$ (Zn Mesotetranitroporphine)

0.5 g ZnP is dissolved in 300 ml $CH_2Cl_2$ and excess $NO_2$ is bubbled through the solution at room temperature for 5 minutes. After stirring for an additional ½ hour the Soret moves from 397 nm to 424 nm. The solvent is removed by evaporation and the solids washed with $H_2O$. TLC shows a single product UV/VIS ($CHCl_3$) 424, 521, 571 nm. Infrared (KBr) $\nu_{N-O}$ 1356 cm$^{-1}$ (strong) and 1541 cm$^{-1}$ (medium).

EXAMPLE 4

$FeP(NO_2)_4Cl$ from $H_2P(NO_2)_4$

The meso-tetranitroporphin iron chloride and salts of other metals such as Mn, Co, Cr and Ru can be made by insertion of the metal chloride, acetate or perchlorate salt into $H_2P(NO_2)_4$ in THF. The $H_2P(NO_2)_4$ is prepared by removal of Zn from $ZnP(NO_2)_4$ using 70% $HClO_4$. 100 mg of $ZnP(NO_2)_4$ is dissolved in 100 ml of $CH_2Cl_2$ containing 10 ml of 70% $HClO_4$. This solution is stirred at room temperature for 1 hour, washed twice with $H_2O$, then neutralized with saturated sodium bicarbonate aqueous solution. The $CH_2Cl_2$ is reduced to dryness. The metal, e.g. Fe, is inserted by adding a 10–50% excess of $FeCl_2$ to a refluxing THF solution of the $H_2P(NO_2)_4$.

EXAMPLE 5

Preparation of Fe Mesotetranitro β-tetraethyl β-tetratrifluoromethyl Porphin Chloride $FeP(NO_2)_4[\beta(Et)_4-(CF_3)_4]Cl$ The complex $H_2P[\beta-(Et)_4\beta-(CF_3)_4]$ is prepared by condensation of β- ethyl-β-$CF_3$-2-hydroxymethylpyrrole in acidic media. It can be metallated with $FeCl_2$ in THF to produce $FeP[\beta-(Et)_4\beta-(CF_3)_4]Cl$. 0.1 g of this complex is dissolved in 150 ml of $CH_2Cl_2$ and an excess of $NO_2$ is bubbled through the solution for 5 minutes producing the tetranitro complex of Fe, $FeP(NO_2)_4[\beta-(Et)_4-\beta-(CF_3)_4]Cl$. The solvent is evaporated, the solid taken up in $CHCl_3$ and chromatographed on alumina.

The invention claimed is:

1. A composition of matter useful as catalyst, comprising compounds having the formula:

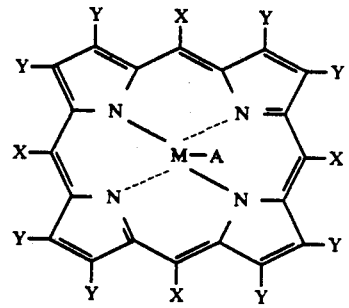

where M is iron, chromium, manganese, ruthenium, copper or cobalt, said X's are nitro, 0 to 3 of said X's are hydrogen, halogen, cyano, hydrocarbon or halocarbon, Y is hydrogen, halogen, nitro, cyano, hydrocarbon or halocarbon, where A is an anion or is absent, said compounds optionally having iron complexes of μ oxo dimers comprising two structures as shown in said formula joined through an M-O-M linkage.

2. A composition according to claim 1 wherein Y is hydrogen, halogen, nitro, cyano, halocarbon, aryl or cycloalkyl.

3. A composition according to claim 2 wherein M is copper and each Y is hydrogen.

4. A composition according to claim 1 wherein A is chloride, bromide, fluoride, hydroxy, cyanide, nitride, thiocyanate, cyanate, methoxy, chlorate, carboxylate.

5. A composition according to claim 1 wherein said compound is said iron complex of μ oxo dimer.

6. An iron complex of mesotetranitroporphyrin or mesotetranitroporphyrin halide.

7. A copper complex of mesotetranitroporphyrin.

8. An iron complex of mesotetranitro β-tetraethyl-β-tetra (trifluoromethyl)porphyrin halide.

9. A composition of matter useful as catalysts, comprising compounds having the formula:

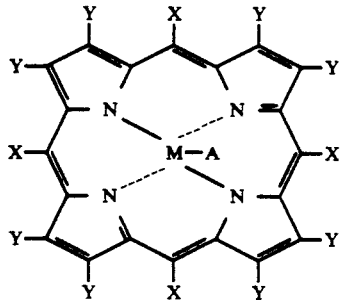

where M is iron, chromium, manganese, ruthenium, copper or cobalt, X is hydrogen, halogen, nitro, cyano, alkyl, cycloalkyl or halocarbon, at least one of said Y's is nitro the remaining Y's are hydrogen, halogen, nitro, cyano, hydrocarbon or halocarbon where A is an anion or is absent, said compounds optionally having iron complexes of μ oxo dimers comprising two structures as shown in said formula joined through an M-O-M linkage.

10. A composition according to claim 9 wherein said remaining Y's are halogen.

11. A composition according to claim 9 wherein each X is fluorocarbon.

12. A composition according to claim 9 wherein A is chloride, bromide, fluoride, hydroxy cyanide, nitride, thiocyanate, cyanate, methoxy, chlorate, carboxylate or azide.

13. A composition according to claim 9 wherein said compound is said iron complex of μ oxo dimer.

14. A composition of matter, useful as a catalyst, an iron complex of mesotetraperfluoroalkyl-β-nitroporphyrin, having 1 to 7 carbon atoms in said alkyl group.

* * * * *